US009364715B2

(12) United States Patent
Qiu

(10) Patent No.: US 9,364,715 B2
(45) Date of Patent: Jun. 14, 2016

(54) SPINE REHABILITATION EXERCISE DEVICE

(71) Applicant: Aiguo Qiu, Ningbo (CN)

(72) Inventor: Aiguo Qiu, Ningbo (CN)

( * ) Notice: Subject to any disclaimer, the term of this patent is extended or adjusted under 35 U.S.C. 154(b) by 25 days.

(21) Appl. No.: 14/240,137

(22) PCT Filed: Jan. 14, 2013

(86) PCT No.: PCT/CN2013/000022
§ 371 (c)(1),
(2) Date: Feb. 21, 2014

(87) PCT Pub. No.: WO2014/063430
PCT Pub. Date: May 1, 2014

(65) Prior Publication Data

US 2014/0378283 A1 Dec. 25, 2014

(30) Foreign Application Priority Data

Oct. 25, 2012 (CN) .......................... 2012 1 0414931

(51) Int. Cl.
*A61F 5/042* (2006.01)
*A63B 26/00* (2006.01)
*A61H 1/02* (2006.01)

(52) U.S. Cl.
CPC .............. *A63B 26/00* (2013.01); *A61H 1/0292* (2013.01); *A61H 1/0296* (2013.01); *A61H 2201/0134* (2013.01); *A61H 2201/1261* (2013.01); *A61H 2201/1284* (2013.01); *A61H 2201/1609* (2013.01); *A61H 2201/1623* (2013.01); *A61H 2201/1664* (2013.01); *A61H 2201/1676* (2013.01); *A61H 2203/0456* (2013.01)

(58) Field of Classification Search
CPC .............. A61F 5/01; A61H 1/00; A61H 1/02; A61H 1/0292; A61H 15/00; A61H 2015/0071; A61H 15/0007; A61H 2201/0134; A61H 2201/0157; A61H 2201/1261; A61H 2201/1284; A61H 2201/1623; A61H 2201/1664; A61H 2203/0456; A63B 2023/006; A63B 21/00109; A63B 22/16; A63B 22/18; A63B 22/208; A63B 26/00
See application file for complete search history.

(56) References Cited

U.S. PATENT DOCUMENTS 2,004,428 A * 6/1935 Davies .................. A61H 15/00 601/118
3,738,653 A * 6/1973 Simpson ................ A63B 67/04 473/475
3,784,148 A * 1/1974 Hill ........................ A47C 3/025 248/582

(Continued)

FOREIGN PATENT DOCUMENTS

WO WO 2014/063430 A1 * 1/2014

*Primary Examiner* — Loan H Thanh
*Assistant Examiner* — Rae Fischer
(74) *Attorney, Agent, or Firm* — Wang Law Firm, Inc.

(57) ABSTRACT

A spine rehabilitation exercise device comprises a soleplate; and an exercise mechanism disposed on the soleplate, wherein the exercise mechanism comprises a sliding mechanism movably disposed on the soleplate; a supporting base movably mounted on top of the sliding mechanism, the supporting base being capable of rocking on top of the sliding mechanism; a pillow mounted on the supporting base; and an elastic assembly disposed between the pillow and the supporting base. The whole device has simple structure, convenient assembly, small and compact volume and good mobility and portability; the device can not only have health care and therapeutic effects on spine, but also be used as a pillow on other occasions, thereby having high practicability and better flexibility in use; moreover, the device is not driven by a power supply, so that it is safer and more reliable to use.

10 Claims, 8 Drawing Sheets

(56) References Cited

U.S. PATENT DOCUMENTS 4,147,828 A * 4/1979 Heckel .................... A63B 6/00
428/314.4
5,897,464 A * 4/1999 Mcleod .................. A63B 23/08
482/132
6,293,625 B1 * 9/2001 Dixon .................... A47C 7/022
297/452.23

* cited by examiner

A-A

B-B

SPINE REHABILITATION EXERCISE DEVICE

RELATE APPLICATIONS

This application is a national phase entrance of and claims benefit to PCT Application for Spine Rehabilitation Exercise Device thereof, PCT/CN2013/000022, filed on Jan. 14, 2013, which claims benefit to Chinese Patent Application 201210414931.7, filed on Oct. 25, 2012. The specifications of both applications are incorporated here by this reference.

FIELD OF THE INVENTION

The present invention relates to a health care equipment, particularly to a human spine rehabilitation exercise device.

DESCRIPTION OF THE PRIOR ART

As an axial skeleton of a human being, spine (also known as backbone), called "the second lifeline of human body" by medical experts, not only has functions of supporting the body and buffering the stress and shock on the body, but also is a support center of chest and abdomen with functions of protecting visceral organs of chest and abdomen and spinal cord, therefore, the importance of the spine to human heath is self-evident.

For most people, one of the main causes of spinal injury is keeping a post unchanged for a long time. For example, people, working over a desk, generally sit in front of a computer for a long time. Keeping the head forward becomes a normal state both in work and life, which brings large loads to the spine; as a result, it is likely to cause spinal abnormality. Spinal abnormality may not only cause neck pain, shoulder pain, back pain and numbness of limb, but also affect blood vessels near the spine and disrupt nerves managing the viscera, thereby resulting in disorder of breath, digestion, circulation and other systemic functions. Consequently, many people are in ailment or sub-health status, and the quality of work and life is influenced seriously.

To prevent and treat various spinal diseases, there has been various health care appliances and medical facilities for massaging the spine in the prior art. For example, U.S. Pat. No. 6,899,688 disclosed a cervical spine massager, the massager has a driving device, two shaft seats are disposed on the driving device, and each of the shaft seats is provided with a shaft lever in connection with a roll sleeve; and when the driving device moves, the roll sleeves can move along the curve of the cervical spine of the user, which meets the requirement of the physiological radian of the human cervical spine, so that the user is allowed to be massaged comfortably. Furthermore, Chinese Utility Model Patent No. CN202342417U (Patent No.: ZL201120385769.1), entitled "Human Spine Curve Massager", disclosed a human spine curve massager, where the human spine curve massager consists of a soleplate, a massage block and a supporting block fixed on the soleplate, and an electronic oscillator; the upper surfaces of the massage block and the supporting block form a curved surface similar to the human spinal curve; and, when a person lies on the massager on his back, the spine may be in a completely relaxed state, at this moment, the tired and sore parts are massaged using the massage block in the presence of high frequency pulse current generated by the electronic oscillator, accompanied by radio wave stimulation for physiotherapy, thereby generating excellent effects in relieving fatigue and pains.

However, the massages described in the above patents have a common problem that they need to be connected to a power supply when in service. The action of the massagers is to be driven by a motor or generated by an electronic oscillator. Once the electronic circuit is damaged or breaks down, the massagers are unable to operate normally so that the service life of the massagers is limited by electronic equipment. Furthermore, a risk of current leakage of the electronic equipment may cause safety problems in service. Second, massagers applying an electronic driving device generally have large size, complicated structure and poor mobility and portability, thereby resulting inflexible use. In addition, when the massagers described in the above patents are in service, generally, the position of a person is kept unmoved relatively while the massage heads on the massagers do reciprocating motion, so that only parts of acupuncture points of cervical spine or spine can be massaged passively, and the active training and exercise to intraspinal nerves and visceral organs in the chest and abdomen cannot be further realized. The effect of comprehensive health care is not ideal. Hence, in order to solve the problems existed in the above patents and achieve the purpose of optimizing the structure and improving the health care effect, such massagers need to be further improved.

SUMMARY OF THE INVENTION

It is an object of the present invention to provide a spine rehabilitation exercise device with simple structure, flexible use and high safety in view of the current situation in the prior art.

For achieving the above stated object, the spine rehabilitation exercise device comprises: a soleplate; and an exercise mechanism disposed on the soleplate, wherein the exercise mechanism comprises a sliding mechanism movably disposed on the soleplate;

a supporting base with an arc-shape bottom surface movably mounted on top of the sliding mechanism, the supporting base being capable of rocking on top of the sliding mechanism and moving horizontally and in line together with the sliding mechanism on the soleplate;

a pillow, with a curve top surface matching a natural physical curvature of human spine, mounted on the supporting base; and an elastic assembly disposed between the pillow and the supporting base, which enables the pillow to have a trend of bouncing upward all the time.

In order to ensure that the exercise device can slide in line on the soleplate and to realize movement limit, preferably, the sliding mechanism further comprises a slider, the slider has a bottom and a limiting mechanism for limiting movement of the slider on the soleplate, the bottom of the slider is provided with a rolling assembly, the supporting base is movably mounted on the slider, and the rolling assembly enables the sliding mechanism to slide in line on the soleplate.

In order to realize the movably connection of the supporting base on the slider and to ensure the normal restoration of the supporting base after rocking, preferably, the supporting base has at least one pin hole, the slider has at least one connecting hole, each pin hole matching a connecting hole, and at least one pin passing through one pin hole and a corresponding connecting hole for connecting the supporting base to the slider, the at least one pin has a head and is fitted with a first spring with two ends, one end of the first spring presses against the head of the at least one pin and other end of the first spring presses against inside of the pin hole, and the first spring enables the at least one pin to move upward when the supporting base rocks and restores the at least one pin to a previous position when the supporting base is standing still.

The in-line movement of the slider on the soleplate may be realized in multiple ways, for example, by matching of slide rails and guide slots, matching of lead screws and screw rods, etc. Preferably, in the present application, a rolling assembly is employed to realize the in-line movement. The rolling assembly comprises at least one ball seating and a plurality of balls placed inside the at least one ball seating, and the bottom of the slider is provided with at least one groove for receiving the at least one ball seating, the at least one ball seating is provided with a plurality of linearly aligned pores, each pore enabling one ball to touch the soleplate. Hence, the rolling contact between the slider and the soleplate may be realized by the balls, so that it is more convenient and strength-saving for the movement of the slider, and the flexibility of the movement of the slider is improved.

In order to prevent the slider from moving outside the soleplate, the route of back-and-forth movement of the slider on the soleplate is limited. Preferably, the limiting mechanism further comprises a stopping block with a shaft hole and a sliding shaft passing through the shaft hole, the stopping block is fixed on the soleplate; and the bottom of the slider is provided with a limiting recess having two end walls for limiting the stopping block when the slider slides on the soleplate, the stopping block and a sliding shaft are disposed within the limiting recess, and two ends of the sliding shaft are positioned at two end walls of the limiting recess. When the slider slides in-line movement on the soleplate, the movement of the slider may be limited as the two end walls of the limiting recess are pressed against the two ends of the stopping block, so that the slider is ensured to perform in-line reciprocating movement on the soleplate within a certain route range.

In order to reduce the direct collision between the limiting recess and the stopping block, lower the noise and prolong the service life of the slider, preferably, the limiting recess further comprises two shockproof pads for pressing against the stopping block, each shockproof pad disposed at one end wall of the limiting recess, and each shockproof pad has a positioning hole for receiving the sliding shaft.

In order to be convenient to adjust the resistance when the slider slides on the soleplate, preferably, the stopping block further comprising a damping adjustment hole is formed at a bottom of the stopping block communicating with the shaft hole, the soleplate is provided with a through hole, and a damper, inserted through the through hole and the damping adjustment hole, for adjusting the gap between the sliding shaft and the shafting hole.

In order to simplify the structure and to be convenient for assembling and disassembling, preferably, the elastic assembly further comprises at least one spring seat with a top and at least one second spring, the top of the at least one spring seat is connected to the pillow, at least one stand column extending downwardly from the at least one spring seat, the supporting base is further provided with at least one cylindrical hole for receiving the at least one stand column, the cylindrical hole further has a positioning column, and the at least one second spring engages the stand column and the positioning column.

In order to make the users more conformable and to avoid injury of the contact part due to too hard pillow, preferably, the pillow further comprises an elastic cushion.

In order to be convenient for placement, avoid any displacement of the device when in service, and to increase the friction between the device and the contacted surface, the soleplate further comprises a bottom and an antiskid cushion attached to the bottom.

Compared with the prior art, in the invention, the whole device has simple structure, convenient assembly, small and compact volume and good mobility and portability; the device can not only have health care and therapeutic effects on spine, but also be used as a pillow on other occasions, thereby having high practicability and better flexibility in use; moreover, the device is not driven by a power supply, so that it is safer and more reliable to use; the spine leans against the pillow to rock back and forth and move horizontally by the movement of the body itself so as to drive the spine and the visceral organs, such as, the viscera in the chest and abdomen, to relax and stretch, so that the blood circulation and metabolism of spinal nerves and related organs is promoted, and the purpose of treatment and rehabilitation and more comprehensive health care can be achieved.

DETAILED DESCRIPTION OF THE PREFERRED EMBODIMENT

Figure 1:
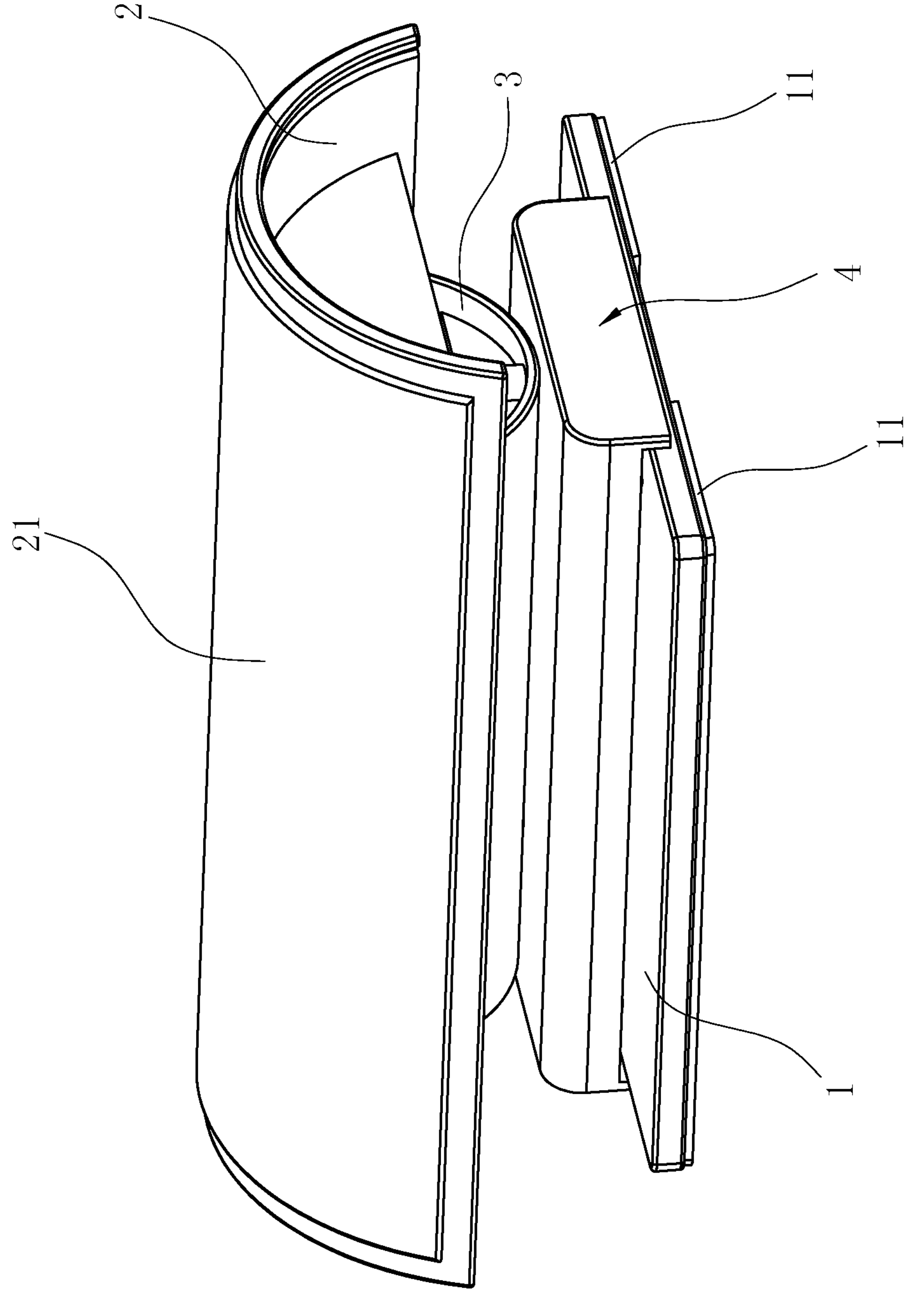
FIG. 1 is a perspective view of an exercise device in accordance with a first embodiment of the present invention.
Figure 2:
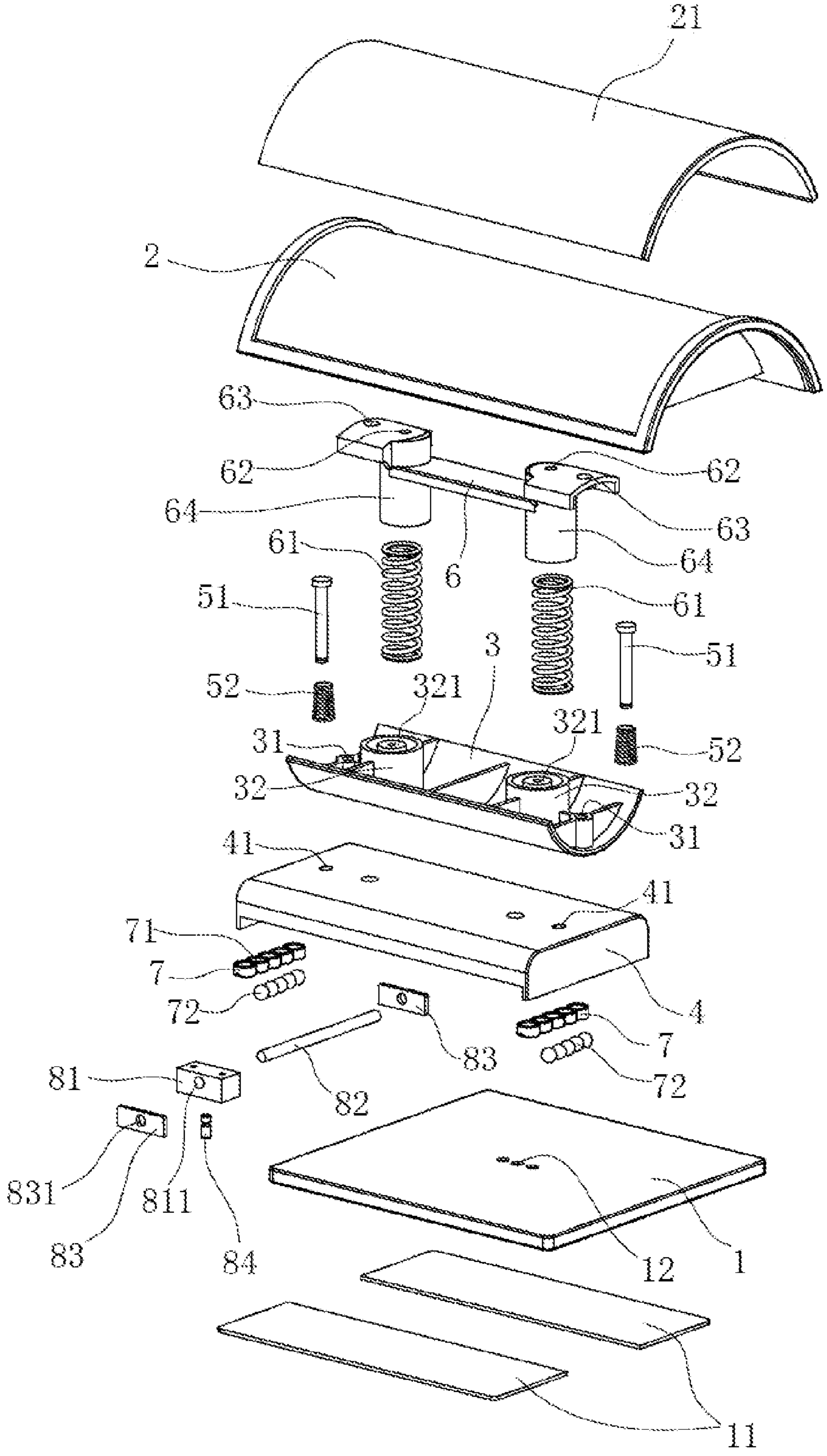
FIG. 2 is an exploded perspective view of the exercise device in accordance with the first embodiment of the present invention.
Figure 3:
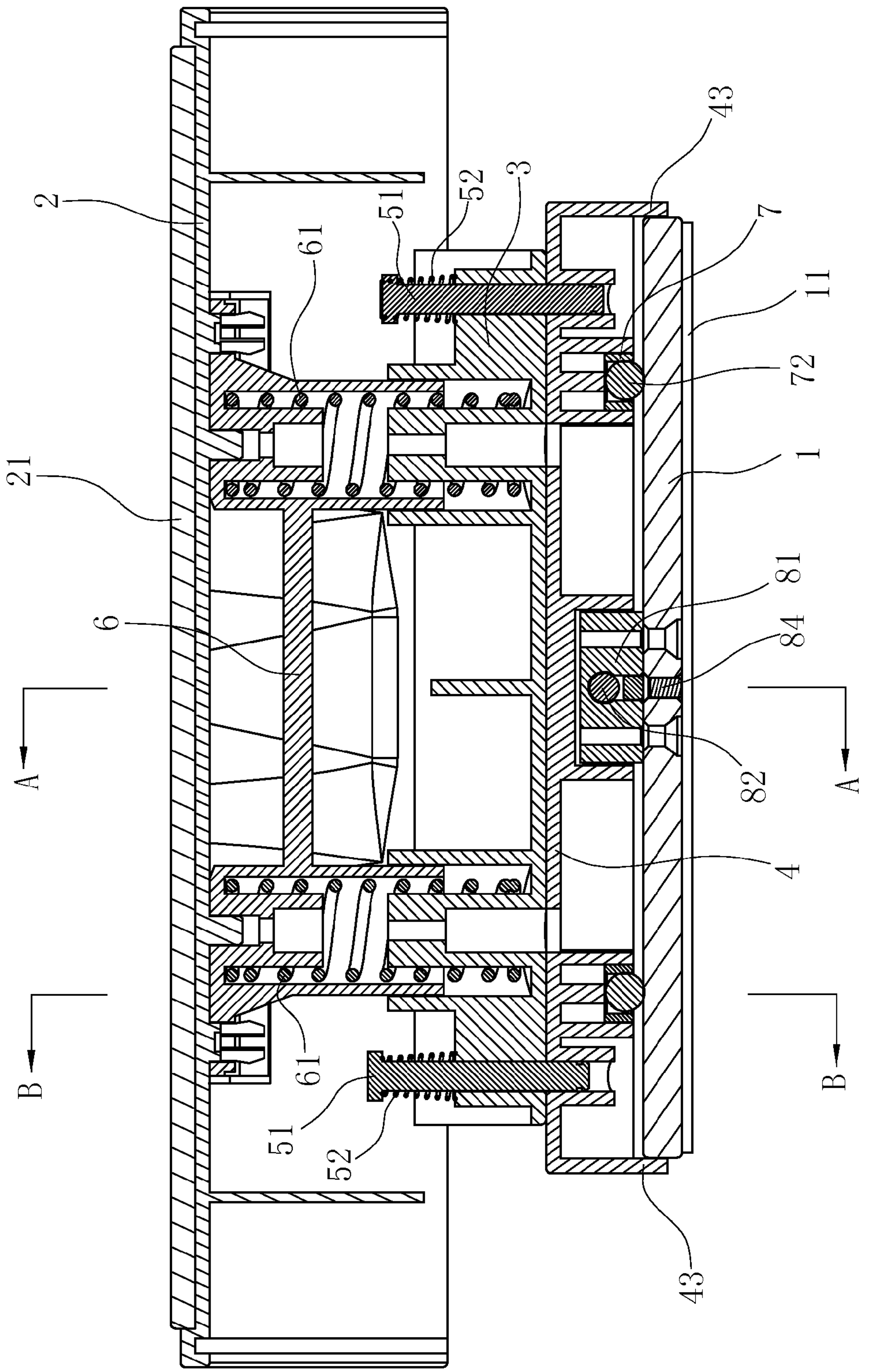
FIG. 3 is a sectional view of the exercise device in accordance with the first embodiment of the present invention.
Figure 4:
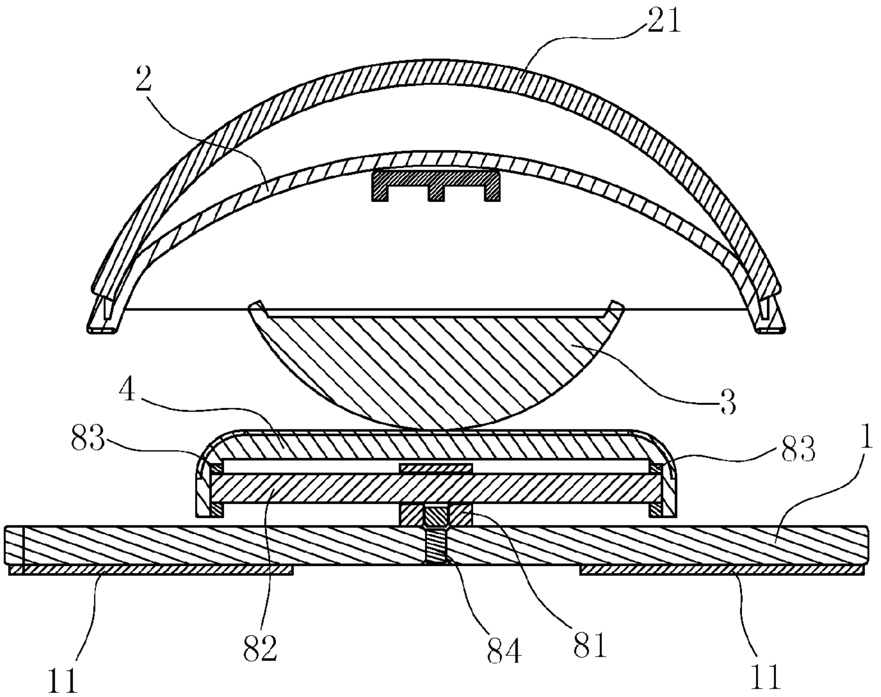
FIG. 4 is a sectional view of line A-A of FIG. 3.
Figure 5:
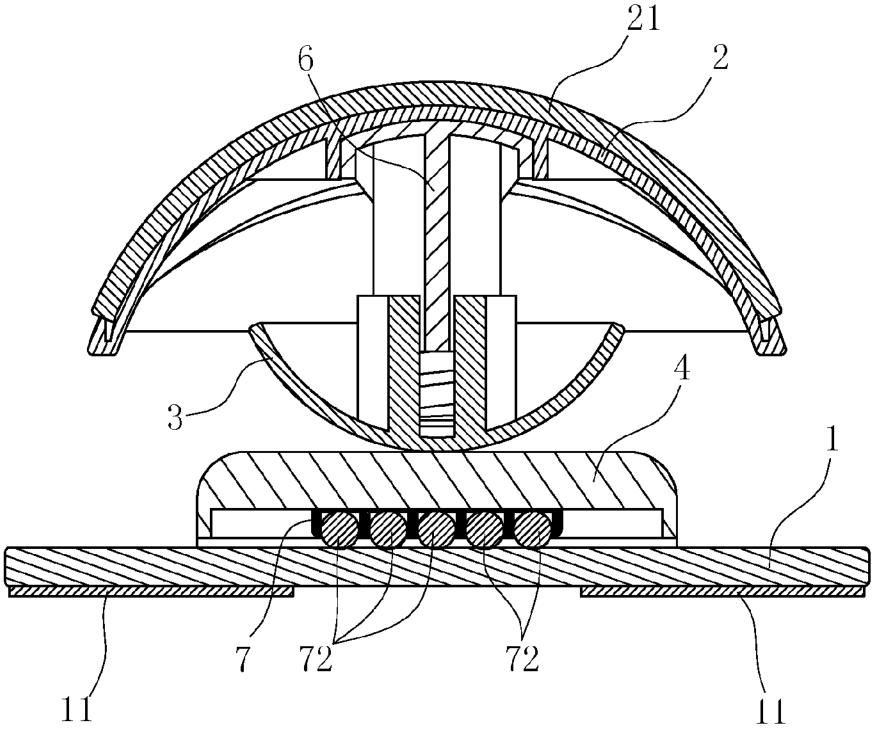
FIG. 5 is a sectional view of line B-B of FIG. 3.
Figure 6:
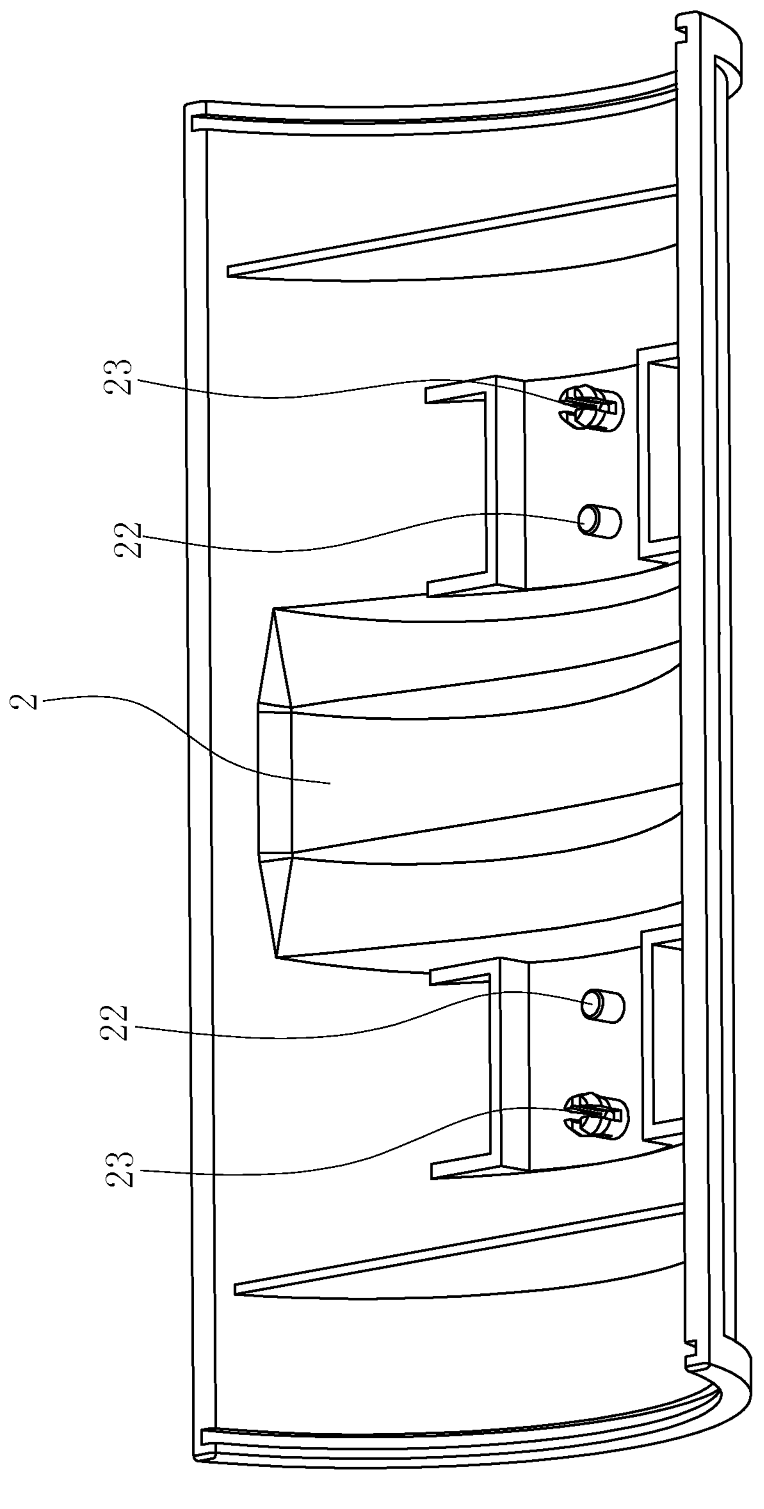
FIG. 6 is a perspective view of the supporting base of the exercise device in accordance with the first embodiment of the present invention.
Figure 7:
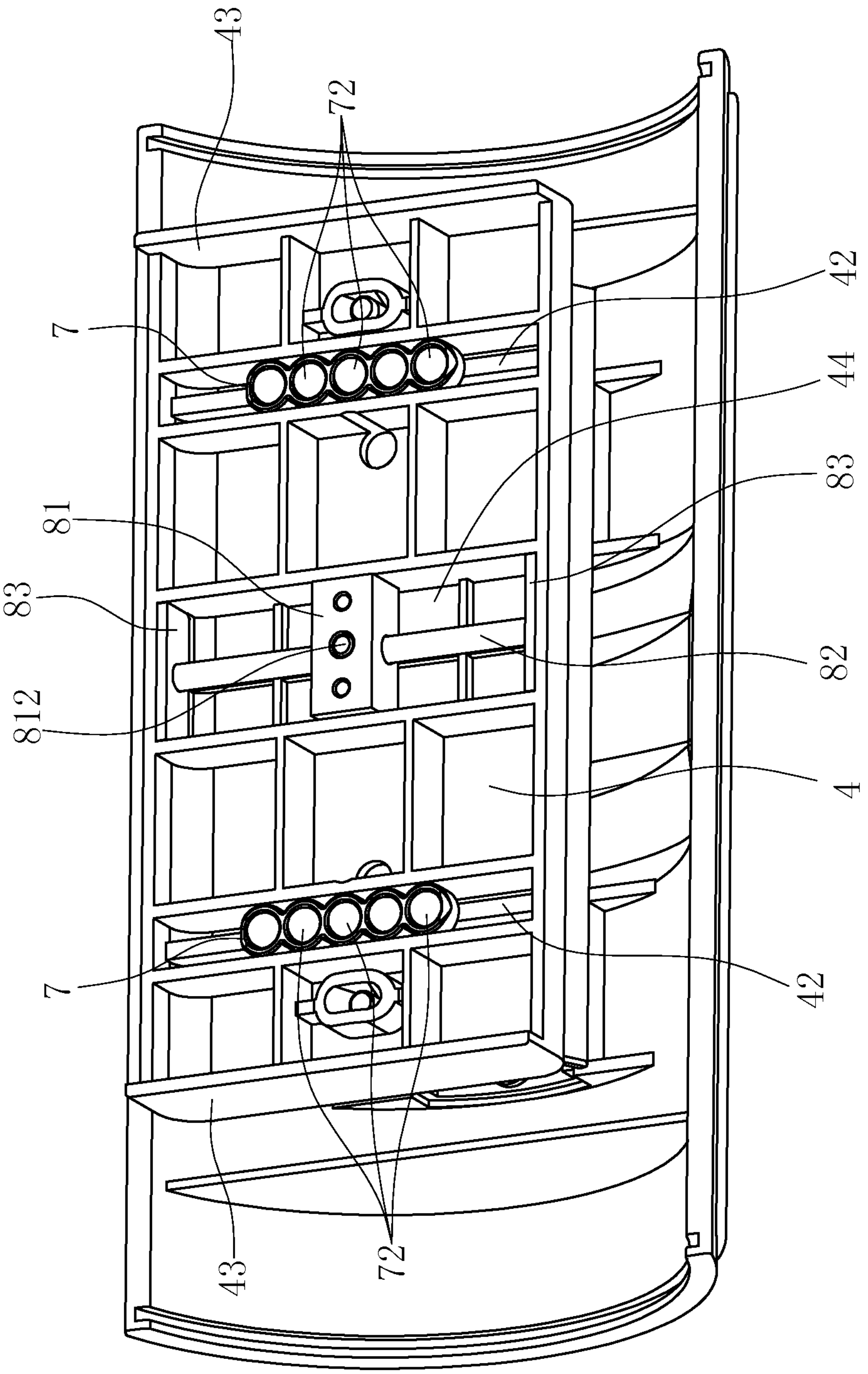
FIG. 7 is a perspective view of the sliding mechanism of the exercise device in accordance with the first embodiment of the present invention.

To enable a further understanding of the innovative and technological content of the invention herein, refer to the detailed description of the invention and the accompanying drawings below:

As shown in FIG. 1 to FIG. 7, in this embodiment, it provides a rehabilitation exercise device for the health care and physiotherapy of the human spine, comprising a soleplate 1 and an exercise mechanism disposed on the soleplate 1. The soleplate further comprising a bottom and an antiskid cushion 11 attached to the bottom, which is capable of avoiding the displacement of the device when in use. The exercise mechanism, in this embodiment, does not need to be driven by a power supply; instead, via a mechanical structure, it realizes movement by the collaboration between the movement of a person and the device. The rehabilitation exercise device may be regarded as an ordinary pillow or a gymnastic apparatus, with convenient operation and safer and more reliable use.

In this embodiment, the exercise mechanism comprises a pillow 2, a supporting base 3 with an arc-shape bottom surface and a sliding mechanism, wherein the sliding mechanism comprises a rectangular slider 4, the slider 4 has a bottom and a limiting mechanism (also known as limiter) for limiting movement of the slider 4, the bottom of the slider 4 is provided with a rolling assembly (also known as roller) which enables the sliding mechanism to slide in line on the soleplate; The cross section of the supporting base 3 is semicircular, and the camber of the supporting base 3 faces the slider 4. The supporting base 3 is capable of rocking on top of the slider 4 and moving horizontally and in line together with the slider 4 on the soleplate 1; a pillow 2, with a curve top surface matching a natural physical curvature of human spine, mounted on the supporting base 3; and an elastic assembly (also known as a bounder) disposed between the pillow 2 and the supporting base 3, which enables the pillow 2 to have a trend of bouncing upward all the time.

In this embodiment, the pillow 2 has a curve top surface matching a natural physical curvature of human spine. The curvature of the curve top surface may be selected according to different exercise parts of the body and different stress. In this embodiment, the curve top surface of the pillow 2 is selected as a curve top surface special for cervical spine. In order to further make the users more comfortable, the pillow 2 further comprises an elastic cushion 21.

The supporting base 3 has two pin holes 31, the slider 4 has two connecting holes 41, each pin hole 31 matching a connecting hole 41, and each pin 51 passing through one pin hole 31 and a corresponding connecting hole 41 for connecting the supporting base 3 to the slider 4, each pin 51 has a head and is fitted with a first spring 52 with two ends, and the first spring 52 may enable the supporting base 3 to rock or to restore, one end of the first spring 52 presses against the head of the pin 51 and other end of the first spring 52 presses against inside of the pin hole 31; the first spring 52 enables the pin 51 to move upward and the pillow 2 to stay in a middle position without inclining when the rehabilitation exercise device is standing still.

The elastic assembly disposed between the pillow 2 and the supporting base 3 comprises a spring seat 6 with a top and two second springs 61, the top of the seat 6 is connected to the pillow 2, wherein the bottom of the pillow 2 is provided with two bosses 22 and two elastic latches 23, the top of the seat 6 is provided with two insert holes 62 capable of fastening the bosses 22 and two lock holes 63 capable of fastening the elastic latches 23; two stand columns 64 extending downwardly from the spring seat 6, the supporting base 3 is further provided with at two cylindrical holes 32 for receiving the stand columns 64, each cylindrical hole 32 further has a positioning column 321. The second springs 61 ensure a proper stress onto the spine when a user is doing exercise, and each second spring 61 engages the stand column 64 and the positioning column 321.

Two sides of the bottom of the slider 4 are provided with two grooves 42, parallel to each other, for receiving the two ball seatings 7, each ball seating 7 can move in line in the corresponding groove 42, the ball seating 7 is provided with a plurality of linearly aligned pores 71 (in this embodiment, the ball seating 7 is provided with five linearly aligned pores), each pore enabling one ball to touch the soleplate 1.

In order to control the movement direction of the slider 4 on the soleplate 1, baffles 43 extending downward are formed on two sides of the slider 4. The distance between the two baffles 43 is rightly matched with the length of the soleplate 1. When the slider 4 moves horizontally, the insides of the baffles 43 can be in rolling touch with the two side edges of the soleplate 1 in the length direction so as to achieve the guide effect.

The limiting mechanism further comprises a stopping block 81 with a shaft hole and a sliding shaft 82 passing through the shaft hole 811, the stopping block 81 is fixed on the soleplate 1 by screw; and the middle part of the bottom of the slider 4 is provided with a limiting recess 44, which is parallel to the groove 42 receiving the ball seating 7, having two end walls for limiting the stopping block 81 when the slider slides on the soleplate, the stopping block 81 and a sliding shaft 82 are disposed within the limiting recess 44; in order to prolong the service life of the stopping block 81, the limiting recess 44 further comprises two shockproof pads 83 for pressing against the stopping block 81, the shockproof pads 83 may eliminate the shock generated during the horizontal movement of the slider 4 to the limit end, and also reduce collision noise, each shockproof pad disposed at one end wall of the limiting recess 44, and each shockproof pad 83 has a positioning hole 831 for receiving the sliding shaft 82; the stopping block 81 further comprises a damping adjustment hole 812 is formed at a bottom of the stopping block 81 communicating with the shaft hole 811, the soleplate 1 is provided with a through hole 12, and a damper 84 is inserted through the through hole 12 and the damping adjustment hole 812, the damper 84 can adjust the gap between the sliding shaft 82 and the shafting hole 811, in order to control the speed and strength of the slider 4 during the horizontal movement, so as to adapt to users of different constitution.

For convenient processing, the pillow 2, the spring seat 6, the supporting base 3 with semicircle bottom surface, the slider 4 and soleplate 1 in this embodiment are all formed by injection molding in one time, while the elastic cushion 21 disposed on the pillow 2 is formed by impact molding in one time. Standard fasteners are preferably used as fasteners (screws, etc.) between all components.

In this embodiment, the curve top surface of the pillow 2, matching a natural physical curvature of human spine, is mainly used for realizing the exercise of cervical spine. When in service, the rehabilitation exercise device is placed on a horizontal plane; a person lies on his back with both lower limbs bent at 90 degrees and both feet spaced apart at an interval equal to the shoulders; and the exercise device is placed below the neck, with the center of the cervical spine facing the center of the curved face of the pillow 2. A new user is better to hold the two ends of the pillow 2 by both hands so as to assist the cervical spine to do horizontal movement back and forth on the camber. When the user lowers his head so that the shoulders go down, the pillow 2 moves upward; and when the user raises his head so that the shoulders and the waist rise up, the pillow 2 moves downward. Each back-and-forth movement of the pillow 2 is a period of exercise. For a new user, the number of the periods of exercise should be increased progressively from less to more, depending on individual difference, such as constitution.

Figure 8:
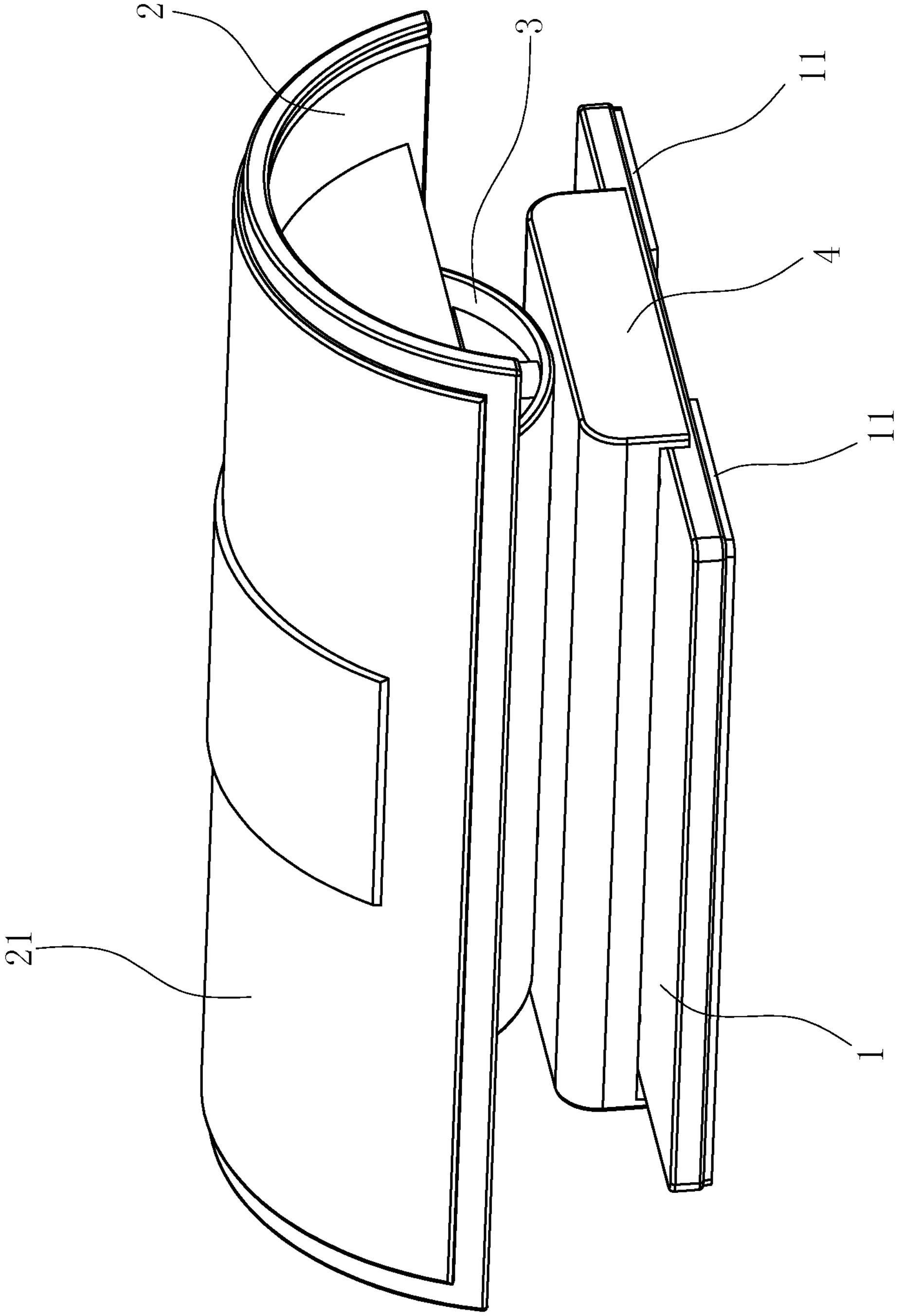
FIG. 8 is a perspective view of an exercise device in accordance with a second embodiment of the present invention.
Figure 9:
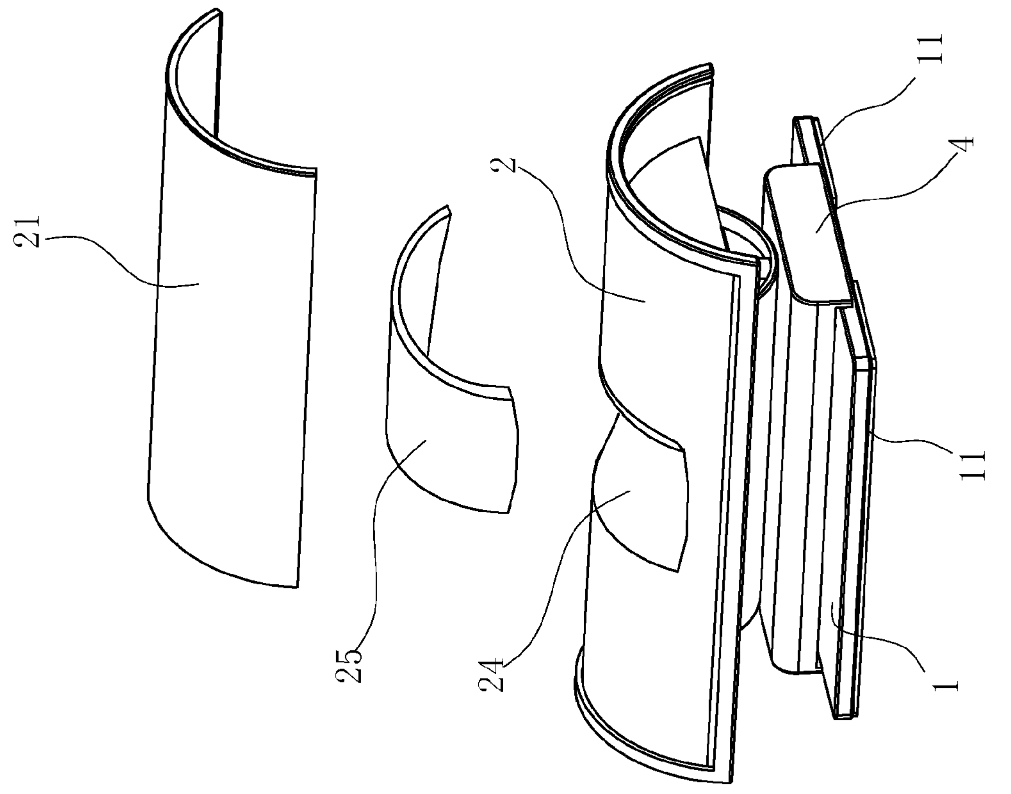
FIG. 9 is an exploded perspective view of the exercise device in accordance with the second embodiment of the present invention.

Embodiment 2, as shown in FIG. 8 and FIG. 9, the difference between this embodiment and Embodiment 1 is that, in this embodiment, the pillow has a curve top surface special for thoracolumbar spine, mainly for the exercise of thoracolumbar spine; and the pillow 2 comprises an elastic cushion 21, wherein the middle part of the curve top surface special for thoracolumbar spine is formed with an arc depression 24 matching spinel evagination. The arc depression 24 is soft and flexible, and the portion of the arc depression 24 is formed with an elastic bump 25 matching the depression in size, so that the outer surface of the elastic cushion 21 forms a block protruding outward. Therefore, a user with thoracolumbar spine kyphosis may feel more conformable when doing exercise and the effect of rehabilitation by exercise may be ensured.

When in service, the rehabilitation exercise device in this embodiment is placed on a horizontal plane, and a person lies on his back with both lower limbs bent at 90 degrees and both feet spaced apart at an interval equal to the shoulders. The specific massage method will be described as below:

From down to up:

(1) Exercise of lumbosacral spine: the rehabilitation exercise device is placed in the center of the waist corresponding to the navel, with the center of the spine facing the center of the pillow. When the jaw and the lower back rise up and the hip goes down, the pillow 2 moves upward; and when the jaw and the lower back go down and the hip rises up, the pillow 2 moves downward. Each back-and-forth movement of the pillow 2 is a period of exercise. For a new user, the number of periods of exercise should be increased progressively from less to more, depending on individual difference, such as constitution.

(2) Exercise of lower thoracic spine: the rehabilitation exercise device is placed under the back at three inches above the navel (four transverse fingers) corresponding to the stomach, with the center of the spine facing the center of the pillow 2. When, the jaw and the shoulders rise up and the waist and the hip go down, the pillow 2 moves upward; and when the jaw and the shoulders go down and the waist and the hip rise up, the pillow 2 moves downward. Each back-and-forth movement of the pillow 2 is a period of exercise. For a new user, the number of periods of exercise should be increased progressively from less to more, depending on individual difference, such as constitution.

(3) Exercise of upper thoracic spine: the rehabilitation exercise device is placed under the chest-back taking the nipple as center, with the center of the thoracic spine facing the center of the pillow 2. When the jaw and the shoulders rise up and the waist and the hip go down, the pillow 2 moves upward; and when the jaw and the shoulders go down and the waist and the hip rise up, the pillow 2 moves downward. Each back-and-forth movement of the pillow 2 is a period of exercise. For a new user, the number of periods of exercise should be increased progressively from less to more, depending on individual difference, such as constitution.

The invention claimed is:

1. A spine rehabilitation exercise device comprising:

a soleplate;

a slider movably disposed on the soleplate and sliding linearly along a sliding shaft attached to the soleplate;

a supporting base with an arc-shaped bottom surface movably mounted on top of the slider, the supporting base being capable of rocking on top of and relative to the slider;

a pillow, with a curved top surface, mounted on the supporting base and capable of moving vertically relative to the supporting base; and an elastic assembly disposed between the pillow and the supporting base, enabling the pillow to move closer to the supporting base and to restore position of the pillow by moving the pillow upward.

2. The exercise device of claim 1, wherein the slider further comprises a bottom and a limiter for limiting movement of the slider on the soleplate, the bottom of the slider is provided with a roller, the supporting base is movably mounted on the slider, and the roller enables the slider to slide linearly along the sliding shaft on the soleplate.

3. The exercise device of claim 2, wherein the supporting base has at least one pin hole, the slider has at least one connecting hole, each pin hole matching a connecting hole, and at least one pin 51 passing through one pin hole 31 and a corresponding connecting hole for connecting the supporting base to the slider, the at least one pin has a head and is fitted with a first spring 52 with two ends, one end of the first spring presses against the head of the at least one pin and other end of the first spring presses against inside of the pin hole, and the first spring enables the at least one pin to move upward when the supporting base rocks and restores the at least one pin to a previous position when the supporting base is standing still.

4. The exercise device of claim 2, wherein the roller comprises at least one ball seating 7 and a plurality of balls 72 placed inside the at least one ball seating, and the bottom of the slider is provided with at least one groove for receiving the at least one ball seating, the at least one ball seating is provided with a plurality of linearly aligned pores, each pore enabling one ball to touch the soleplate.

5. The exercise device of claim 2, wherein the limiter further comprises a stopping block 81 with a shaft hole 811 and the sliding shaft 82 passing through the shaft hole, the stopping block is fixed on the soleplate; and the bottom of the slider is provided with a limiting recess having two end walls for limiting the stopping block when the slider slides on the soleplate, the stopping block and a sliding shaft are disposed within the limiting recess 44, and two ends of the sliding shaft are positioned at two end walls of the limiting recess.

6. The exercise device of claim 5, wherein the limiting recess further comprises two shockproof pads 83 for pressing against the stopping block, each shockproof pad disposed at one end wall of the limiting recess, and each shockproof pad has a positioning hole 831 for receiving the sliding shaft 82.

7. The exercise device of claim 5, wherein the stopping block further comprising a damping adjustment hole 812 is formed at a bottom of the stopping block communicating with the shaft hole, the soleplate is provided with a through hole 12, and a damper 84, inserted through the through hole and the damping adjustment hole, for adjusting the gap between the sliding shaft and the shafting hole.

8. The exercise device of claim 1, wherein the elastic assembly further comprises at least one spring seat with a top and at least one second spring 61, the top of the at least one spring seat is connected to the pillow, at least one stand column 64 extending downwardly from the at least one spring seat, the supporting base is further provided with at least one cylindrical hole for receiving the at least one stand column, the at least one second spring being enclosed by at least one stand column and the at least one cylindrical hole, the cylindrical hole further has a positioning column, and the at least one second spring engages the stand column and the positioning column.

9. The exercise device of claim 8, wherein the pillow further comprises an elastic cushion.

10. The exercise device of claim 8, wherein the soleplate further comprising a bottom and an antiskid cushion 11 attached to the bottom.

* * * * *